United States Patent [19]
Millar

[11] Patent Number: 5,191,898
[45] Date of Patent: Mar. 9, 1993

[54] METHOD AND ASSEMBLY FOR MEASURING INTRACRANIAL FLUID CHARACATERISTICS

[75] Inventor: Huntly D. Millar, Houston, Tex.

[73] Assignee: Millar Instruments, Inc., Houston, Tex.

[21] Appl. No.: 878,858

[22] Filed: May 5, 1992

Related U.S. Application Data

[62] Division of Ser. No. 602,152, Oct. 22, 1990, Pat. No. 5,117,836.

[51] Int. Cl.$^5$ .............................................. A61B 5/00
[52] U.S. Cl. ...................................... 128/748; 604/8; 604/160; 604/161
[58] Field of Search ............... 128/748, 774, 760; 606/108, 222, 223, 224, 148, 150; 604/8, 27, 93, 158, 160, 161, 164, 166, 264, 272, 280, 282, 283, 284

[56] References Cited

U.S. PATENT DOCUMENTS

| | | | |
|---|---|---|---|
| 4,114,603 | 9/1978 | Wilkinson | 128/748 |
| 4,147,161 | 4/1979 | Ikebe et al. | 128/748 |
| 4,601,724 | 7/1986 | Hooven et al. | 623/66 |
| 4,666,438 | 5/1987 | Raulerson | 604/272 |
| 4,883,474 | 11/1989 | Sheridan et al. | 604/280 |
| 4,901,731 | 2/1990 | Millar | 128/675 |
| 4,903,707 | 2/1990 | Knute et al. | 128/748 |

FOREIGN PATENT DOCUMENTS 9105575  5/1991  PCT Int'l Appl. ................. 128/748

OTHER PUBLICATIONS

Gaab, Michael R. et al., "Monitoring Intracranial Pressure," *Encyclopedia of Medical Devices*, vol. 3, pp. 1961-1983, 1988.

Noce, Joseph P., "Intracranial Pressure Monitoring," *Biomedical Instrumentation and Technology*, pp. 2-3, Feb. 1990.

*Primary Examiner*—Max Hindenburg
*Assistant Examiner*—Guy V. Tucker
*Attorney, Agent, or Firm*—Arnold, White & Durkee

[57] ABSTRACT

A method and assembly is provided which allows measurement of intracranial fluid charateristics at the intracranial region of the brain. The invention contemplates a method of implanting a ventricular catheter having one end residing in the ventricular region and the other end exiting the cranial region at a distal location. A grooved needle allows placement of a transducer tipped catheter and rerouting of both the ventricular, in-dwelling catheter and the transducer tipped catheter placed within the in-dwelling catheter. Intracranial fluid characteristics are monitored by an electrically coupled distal monitor. Further, access to the intracranial fluid is also provided to allow either short-term or long-term withdrawal or injection of intracranial fluid.

21 Claims, 4 Drawing Sheets

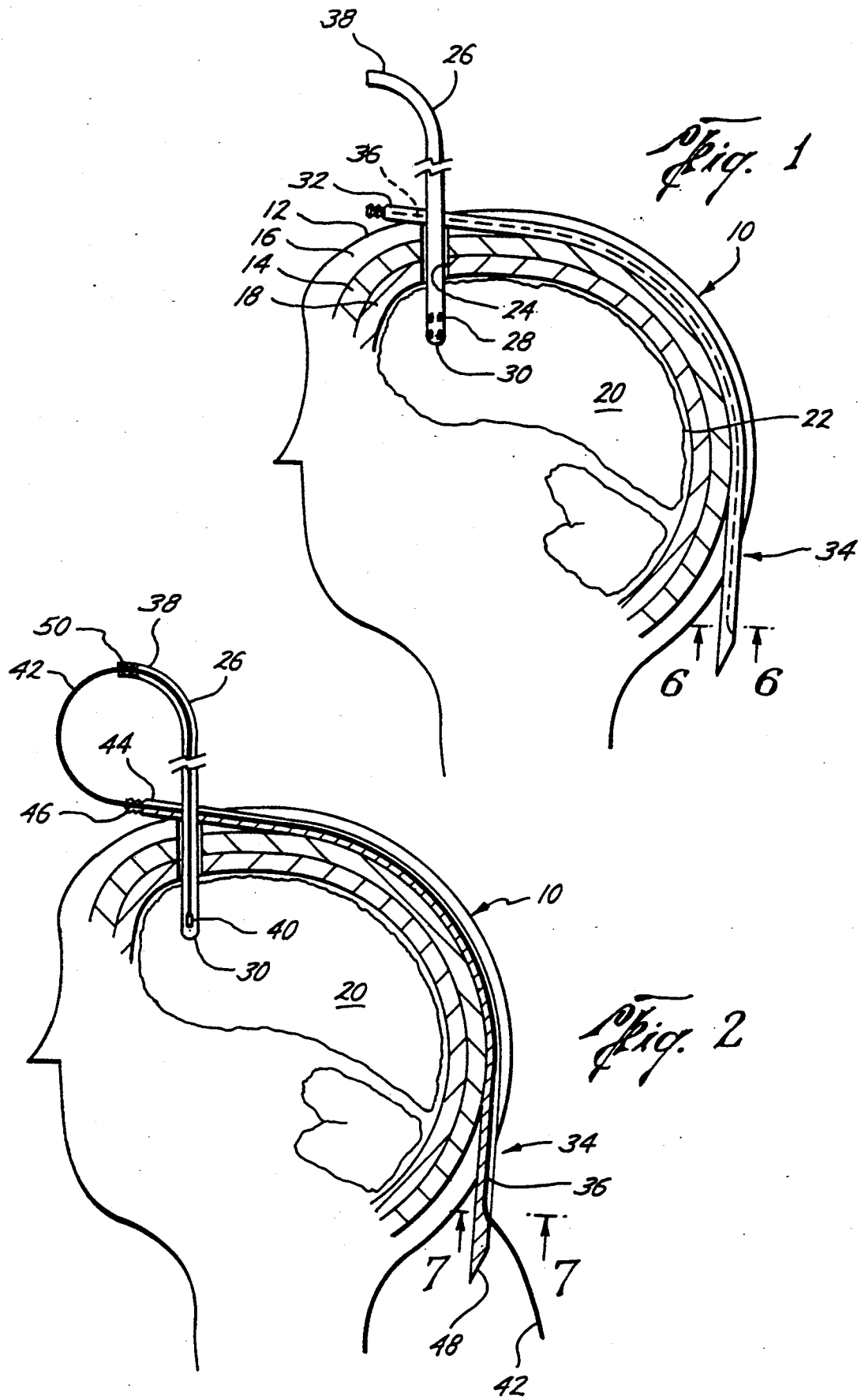

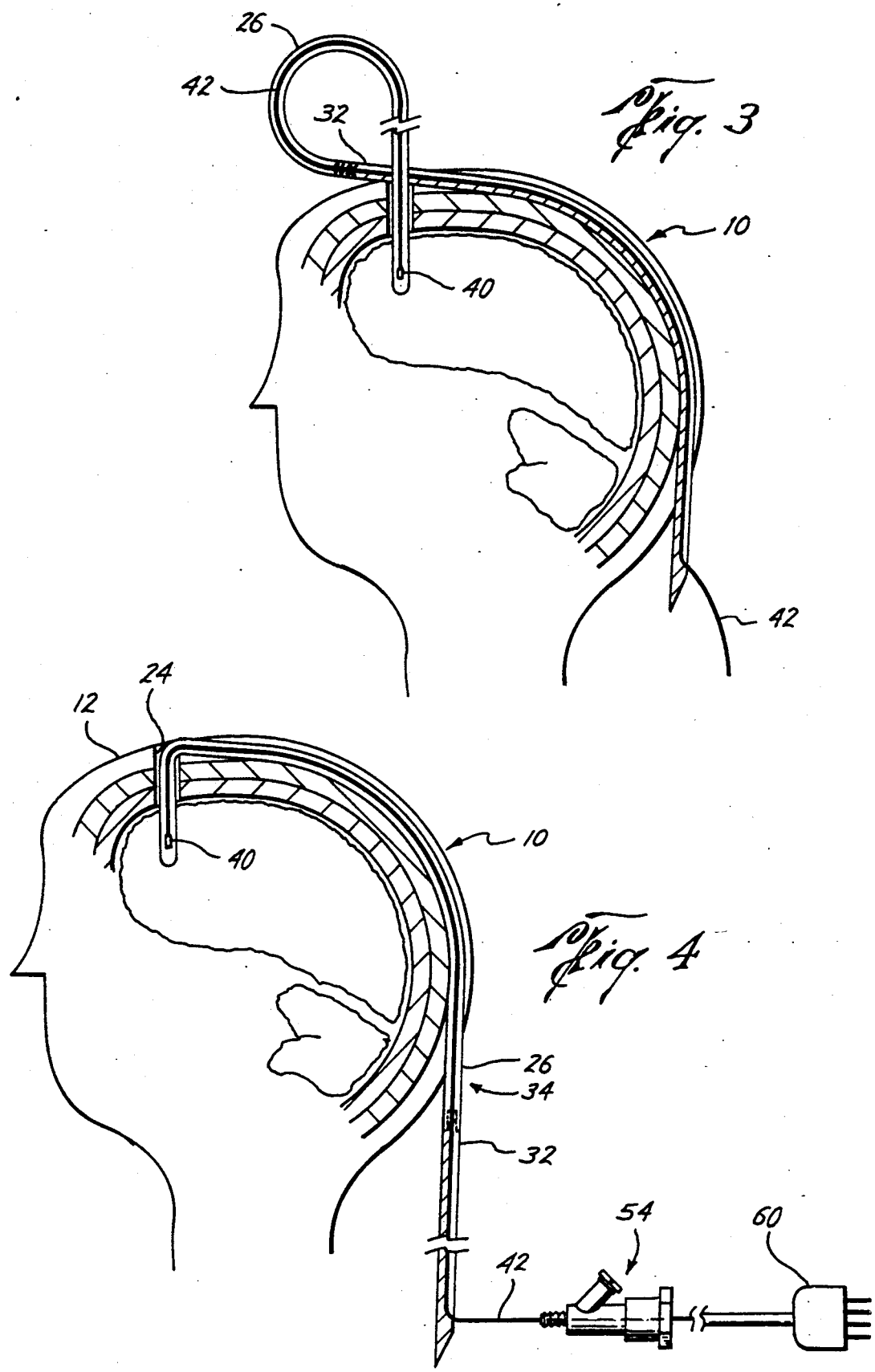

METHOD AND ASSEMBLY FOR MEASURING INTRACRANIAL FLUID CHARACATERISTICS

This is a division of application Ser. No. 07/602,152 filed Oct. 22, 1990 and issued at U.S. Pat. No. 5,117,836 on Jun. 2, 1992.

BACKGROUND OF THE INVENTION

1. Field of the Invention

This invention relates to a method and apparatus for measuring intracranial fluid characteristics. In particular, the method comprises a ventricular catheter which can be positioned into a ventricle of the brain having a transducer tipped catheter positioned at one end of the catheter for measuring fluid compositions, hemodynamics and pressure waveforms of intracranial fluid. A groove placed within a needle retains the transducer tipped catheter and underlying wires and may also provide a

2. Description of the Relevant Art

Cerebral spinal fluid (CSF) circulating within the subarachnoid space between the arachnoid matter and pia matter produces intracranial pressure. CSF exerts pressure on the meningeal membranes as well as on the brain itself. While CSF circulates in the subarachnoid space, it also exists in a ventricle of the brain.

Often it is desirable to measure the CSF pressure in the subarachnoid space or ventricular space whenever the rate of CSF production exceeds resorption. When production does exceed resorption, there is a pressure increase of the CSF causing intracranial pressure (ICP).

Typically, there exists numerous methods in which ICP is monitored. A common method of measuring ICP is to install a subarachnoid screw (bolt) within a hole or burr drilled through the skull. The screw is placed into the subarachnoid space without penetrating the dura residing underneath the skull. A pressure transducer is then attached to the outer end of the screw and monitoring can then proceed. The major advantage of this subarachnoid screw technique is that the dura or cerebrum is not penetrated and therefore subjects the patient to less risk of infection. A major disadvantage in the subarachnoid screw technique is that the bolt can sometimes become occluded leaving false pressure readings at the transducer. Furthermore, because readings are taken in the subarachnoid space external to the dura, fluid pressure is not taken directly where the pressure exists within the brain. Namely, subarachnoid pressure is indirect and sometime yields inaccurate pressure compared to that which exists in the brain tissue underneath the dura. Unless the pressure is taken directly within the ventricular brain matter itself, readings in the subarachnoid space are often susceptible to artifacts and generally less preferred than direct ventricular methods. Often, when drilling the burr hole necessary for placing the screw, pieces of bones remain positioned between the pressure transducer and the pressure source thereby causing artifacts or false, dampened pressure readings.

In an effort to overcome the problems associated with subarachnoid screws, subdural screws are often used by placing the screws through the burr hole to a point underneath the dura matter. Although the subdural screw provides a more accurate pressure sensor than does the epidural screw, it is more intrusive and may subject the patient to infection. The main disadvantage with the subdural screw is that in the case of critically elevated pressures this method fails due to compression of the subarachnoid space (loss of fluid coupling). Furthermore, when acute brain swelling occurs, the pressure at the surface of the brain is generally higher than the pressure inside the ventricle. Thus, while subdural screws achieve more accurate pressure readings than epidural screws, subdural screws still cannot achieve high fidelity readings found in placing the pressure transducer directly into the ventricular region.

While direct placement of a transducer into the ventricle allows accurate pressure readings inside the brain, ventricle placement is highly intrusive and leaves the patient susceptible to infection at the point of insertion. Ventricular placement requires penetration of the skull via a burr hole and insertion of the ventricular transducer through the burr hole and into the ventricle of the brain. The presence of a direct pathway through the burr hole opening from an outside environment directly into the brain ventricle causes substantial risk of infection entering through the burr hole.

In order to alleviate the risk of infection, subdermal routing of the in-dwelling, ventricular catheter is often necessary. Instead of allowing the ventricular catheter to exit the scalp directly above the burr hole, the catheter is routed or redirected from the outer extremity of the burr hole just below the scalp to a distal location. Once the rerouting is achieved, the scalp and underlying tissue is closed over the burr hole or passage thereby leaving no direct path for contamination to enter the burr hole. If contamination is to enter the burr hole, it must travel from the distal exit point of the catheter and along the catheter to the burr hole.

Although distally routed ventricular catheters help reduce the risk of infection entering the burr hole passage, typical catheters placed within the ventricle have a fluid-filled path or fiber-optic signal lines. When rerouting the ventricular catheter, the fluid-filled path or fiber-optic signal lines can become crimped. Crimping or pinch-off occurring during subdermal rerouting often causes a reduction in signal integrity. Fluid-filled paths or fiber-optic signal lines must the handled with care and cannot be sharply redirected or routed to distal location as is often necessary in intracranial ventricular catheter routing application. Accordingly, conventional fluid-filled or optic transducers of the present art produce false or inaccurate pressure readings caused by pinch-off during subdermal routing.

SUMMARY OF THE INVENTION

The problems outlined above are in large part solved by the method and assembly of the present invention. That is, the transducer tipped catheter and/or the surrounding ventricular catheter can be subdermally routed to reduce the risk of infection without incurring pinch-off problems associated with conventional art. A transducer tipped catheter and attached wires can be directed through a groove placed along a subdermally positioned steel needle and down into a burr hole passage or into the in-dwelling ventricular catheter placed within the burr hole. A preferred embodiment comprises direct placement of transducer tipped catheter into the burr hole. Conversely, an alternative preferred embodiment comprises placement of transducer tipped catheter into an in-dwelling ventricular catheter placed in the burr hole. In the alternative preferred embodiment, a steel needle can be drawn through a distal location thereby rerouting the proximal end of the ventricular catheter from an area near the burr hole passage to a distal location without crimping the enclosed transducer tipped catheter. The wires associated with the current pressure transducer can therefore be sharply rerouted to a distal location without incurring loss in transducer signal integrity. The subdermally positioned, grooved steel needle of the present invention is particularly appropriate for drawing both the ventricular in-dwelling catheter and transducer tipped catheter through a confined space regardless of the amount of reroute bending.

Broadly speaking, the present invention contemplates a preferred method of measuring intracranial fluid characteristics by creating a passage into a cranial cavity having the fluid pressure; placing a grooved needle subdermally from the passage to a distal location; positioning a transducer tipped catheter from the distal location through the grooved needle and into the passage; removing the needle; covering the passage over the transducer tipped catheter; and, sensing the intracranial fluid characteristics transmitted from the transducer tipped catheter. According to the preferred embodiment, the distal end of transducer tipped catheter can be inserted directly into the passage via the grooved needle. Thus, the transducer tipped catheter and connected wires are positioned through the groove of the grooved needle and directly into the passage. The transducer tipped catheter can be placed anywhere along the passage. In addition, the transducer tipped catheter can be placed at the base of the burr hole either at the outer surface of the dura matter between the dura and the skull or, preferably, underneath the dura and into a ventricular region. By utilizing the longitudinally placed groove along the grooved needle, the transducer tipped catheter can be placed directly into the passage subdermally from a distal location either with or without a stylet or pushrod.

Broadly speaking, the present invention also contemplates an alternative preferred embodiment or method of measuring intracranial fluid pressure by inserting the distal end of transducer tipped catheter into an in-dwelling ventricular catheter placed within the burr hole passage. The steps of the alternative preferred embodiment comprising creating a passage into a cranial cavity having the fluid pressure, and inserting an in-dwelling ventricular catheter into the passage with the distal end residing in the cranial cavity and having openings therein. Next, a grooved needle is placed subdermally from the passage to a distal location. A transducer tipped catheter is then positioned from the distal location through the grooved needle and into the in-dwelling catheter. Next the in-dwelling catheter is connected to one end of the needle and the other end of the needle is drawn out the distal location to re-route the in-dwelling catheter. The needle is then removed and a covering is placed over the in-dwelling catheter at the passage location. The intracranial fluid characteristics can then be sensed by a monitor connected to the transducer tipped catheter.

A preferred embodiment of the present invention comprises cutting an opening through scalp and tissue and boring a hole through the underlying bone of the skull. An opening can then be created through underlying dura matter and into the cranial cavity. The cranial cavity may be a ventricular region.

An alternative embodiment to the present invention comprises cutting an opening through scalp and tissue and boring a hole within the opening and through underlying bone and into the cranial cavity. The cranial cavity may be an epidural region.

It is important to note that when positioning a transducer tipped catheter from the distal location through the grooved needle and into the in-dwelling catheter, that the needle reside from a point immediately adjacent the passage underneath the scalp (subdermally) to an exit point substantially distal from the passage.

The present invention also contemplates an assembly for measuring the fluid characteristics in a region of intracranial fluid comprising a flexible in-dwelling catheter having a proximal end and a distal end, wherein the distal end includes a plurality of openings; means for inserting the distal end of the in-dwelling catheter into the intracranial fluid; a grooved stainless steel needle having a proximal end removably attachable to the proximal end of the in-dwelling catheter and a distal end having a beveled point. The needle is placed distal end first subdermally from the burr hole to a distally located exit point. A transducer tipped catheter is dimensioned to be positioned through the exit point of the groove and into the distal end of the in-dwelling catheter. Means is provided for connecting the needle to the proximal end of the in-dwelling catheter and for drawing the needle and the proximal end of the in-dwelling catheter out the exit point. Additional means is provided for removing the needle from wires connected to the transducer tipped catheter and for removing the needle from the proximal end of the in-dwelling catheter. A covering of scalp can be placed over the in-dwelling catheter at the burr hold to substantially reduce the risk of infection. A monitor is electrically connected to the wires of the transducer tipped catheter for reading, storing and analyzing fluid characteristics such as chemical content, pressure, hemodynamics and waveform responses of the intracranial fluid.

The present invention additionally contemplates the in-dwelling catheter comprises radiopaque, flexible silicone rubber tubing open at the proximal end to accommodate smaller diameter transducer tipped catheter and closed at the distal end except for a plurality of small openings. The proximal end of the needle comprises a male fitting with snap-fit serrations, detents or threads. The proximal end of the in-dwelling catheter comprises a female fitting with snap-fit serrations, detents or threads. The female fitting is releasably coupleable with the male fitting. A stylet may be included for inserting the in-dwelling catheter into the intracranial fluid. Additionally, the present invention includes adapter means attached by a Luer-Lok coupling to the proximal end of the in-dwelling catheter. Adapter means allows access to the intracranial fluid within the in-dwelling catheter while also preventing contamination from entering the in-dwelling catheter at the point where wires exit the adapter body.

It is important o note that the transducer tipped catheter comprises a strain gauge and electrically connected wires for measuring the amount of deflection of the strain gauge in terms of electrical signals or impulses traveling through the wires from the strain gauge to a distal location where they are received by a reader or monitor.

BRIEF DESCRIPTION OF THE DRAWINGS

FIG. 1 represents a fragmentary anatomical sectional view of the cranial region with the ventricular in-dwelling catheter and subdermally grooved needle implanted therein;

FIG. 2 is a fragmentary anatomical sectional view of the cranial region with a transducer tipped catheter positioned within the in-dwelling catheter and the grooves of the needle;

FIG. 3 is a fragmentary anatomical sectional view of the cranial region with the ends of the ventricular in-dwelling catheter and grooved needle connected;

FIG. 4 is a fragmentary anatomical sectional view of the cranial region with the distal end of the ventricular in-dwelling catheter drawn through the subdermal passage created by the grooved needle;

DESCRIPTION OF THE PREFERRED EMBODIMENTS

Figure 5:
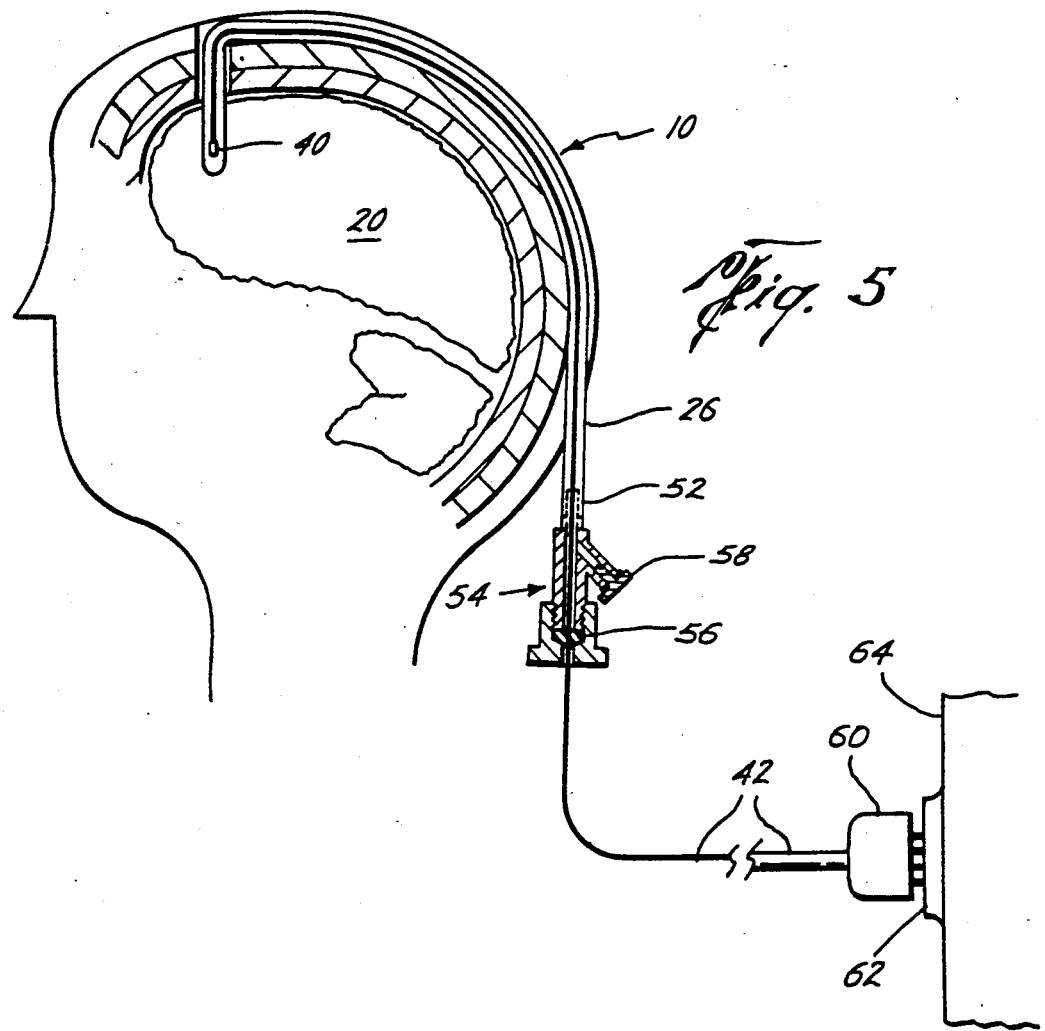
FIG. 5 is a fragmentary anatomical sectional view of the cranial region with the needle removed from the ventricular indwelling catheter and adapter and monitor attached thereto.

Turning now to the drawings, FIG. 1 illustrates an anatomical side view of a human cranial region 10. The cranial region is surrounded by a scalp 12 including skin and/or tissue. Underneath scalp 12 is bone or skull 14. Shown external to skull 14 and internal to scalp 12 is galea 16, referred herein as the subdermal region. Contained underneath or internal to skull 14 is a dura region 18. Underneath dura 18 is brain 20 generally surrounded by cerebral spinal fluid 22.

A passage 24 through scalp 12, galea 16, skull 14, dura 18 and into brain 20 is formed by first making a standard cutaneous exposure of the skull at the appropriate passage location via a scalpel or other cutting means. Next, a burr hole is then formed through skull 14, galea 16 and dura 18 by conventional drilling means. A ventricular, in-dwelling catheter 26 having a plurality of small openings 28 at the distal end 30 of catheter 26 is inserted through passage 24. Distal end 30 is gently inserted by conventional means (possibly with a pushrod or stylet) into the passage or burr hole. Proximal end 30 of catheter 26 is initially configured outside cranial region 10 as shown in FIG. 1.

A solid needle 32, preferably made of a bent or bendable stainless steel material, is inserted along the subdermal region, or galea 16, from passage 24 to a distal region 34. Needle 32 can be of any length provided however that needle 32 is long enough to extend from passage 24 to a desired distal region 34. Distal region 34 is an exit point from which needle 32 exits from the subdermal region outside cranial region 10. Distal region 34 can be located either on the cranial region or at a point substantially distant from the cranial region to thereby operate as a shunt for directing intracranial fluid back into the vascular system.

Figure 6:
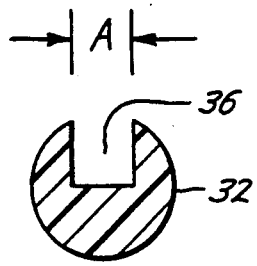
FIG. 6 is a sectional view of the grooved needle taken along line 6—6 of FIG. 1.
Figure 7:
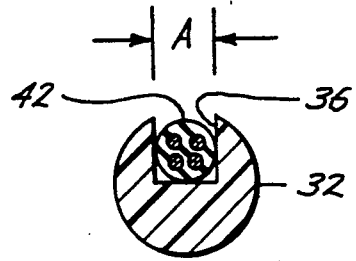
FIG. 7 is a sectional view of the grooved needle taken along line 7—7 of FIG. 2.

Placed along the longitudinal axis of needle 32 is a groove 36 (shown as dotted line in FIG. 1). Needle 32 can be of a disposable stainless steel material and is preferably 7 to 8 inches long with approximately ⅛ inch diameter. Groove 36 extends radially from approximately the center of needle 32 to the outer perimeter of the needle (see FIGS. 6 and 7). Dimension A shown in FIGS. 6 and 7 of groove 36 is preferably 3/64 inch. It is to be appreciated that although 7 to 8 inches is the preferred length and ⅛ inches is the preferred diameter of needle 32, any length or diameter can be utilized provided the length and diameter is sufficient for the specific application. Furthermore, dimension A of groove 36 can be greater than or less than 3/64 inch depending upon the diameter of the accommodated elongated member (e.g., electrical wire).

Ventricular in-dwelling catheter 26 is preferably made of a silicone rubber material open at proximal end 38 and substantially closed at distal end 30. The silicone rubber material is sufficiently flexible so that catheter 26 can be bent or flexed toward needle 32 as will be discussed below. Openings 28 are of any sufficient size which allow intracranial fluid to pass from brain 20 to the inside of catheter 26 after distal end 30 is placed. Openings 28 are sized to prevent clotting if periodically rinsed with a sterile saline solution.

FIG. 2 illustrates a transducer tipped catheter 40 placed within distal end 30 of in-dwelling catheter 26. Electrically coupled and arranged within the proximal region of catheter 40 is at least one flexible electrical conductor or numerous wires 42. Wires 42 within catheter 26 extend within groove 36 of needle 32. After catheter 26 and needle 32 are positioned, as shown in FIG. 1, transducer tipped catheter 40 is configured to reside within distal end 30 by advancing the transducer tipped catheter through groove 36 at distal region 34. Transducer tipped catheter 40 is pushed into groove 36 at distal region 34 to exit groove 36 at proximal end 44 of needle 32. Subsequently, transducer tipped catheter 40 is further advanced into proximal end 38 of in-dwelling catheter 26 until it resides in distal end 30 of catheter 26. Preferably, transducer tipped catheter 40 is approximately 2-3 French in diameter and in-dwelling catheter 26 is 7-10 French is diameter. However, it is to be appreciated that catheters 26 and 40 can be of any diameter provided that catheter 40 can be quickly and easily placed within catheter 26. Catheter 40 is dimensioned to reside in fairly loose fit within the inner diameter of catheter 26.

Placed at proximal end 44 of needle 32 are releasable coupling means 46. Coupling means 46 comprises male thread, detents or serrations adapted to releasably secure within female threads, detents or serrations at distal end 38 of catheter 26. Conversely, at distal region 34, needle 32 includes a beveled, sharpened end 48. Sharpened end 48 allows cutting insertion through the subdermal region from passage 24 to distal region 34.

FIG. 3 illustrates coupling between the proximal end of needle 32 and proximal end 38 of catheter 26. Coupling can be achieved by snap-fit pushing together between male coupling means 46 and female coupling means 50. Serrations or detents are preferably placed upon male coupling means 46 and female means 50. Serrations or detents match to provide quick and easy snap-fit arrangement between needle 32 and catheter 26. Threads may be used to provide rotatable engaging fit. It is preferred that a snap-fit be utilized by simply pushing male coupling means 46 securely into female coupling means 50. Any form of catch or detent which can be releasably engaged is within the scope of this invention.

Once needle 32 and catheter 26 are coupled, transducer catheter containing wires 42 are positioned along groove 36 of needle 32 and into the hollow cavity of catheter 26. By having groove 36 extend along the entire proximal end of needle 44 as well as substantially the entire length of needle 32, a passage is made from the external groove downward into the coupled distal end 38 inner cavity of catheter 26. Thus, the outer surface of catheter 40 and underlying wires 42 remain continuous from distal region 34 to the tip of transducer tipped catheter 40.

Once needle 32 and catheter 26 are connected, needle 32 is drawn through the subdermal region and out of the cranial region at distal region 34 as shown in FIG. 4. As needle 32 is drawn, connected catheter 26 follows along the subdermal path created by needle 32 and out the exit point 34. After catheter 26 is fully drawn, it resides subdermally for the entire length of catheter 26 except for the portion which extends into the ventricular region and a small portion which extends from exit region 34. Because catheter 26 is subdermally placed and routed from passage 24 to exit region 34, risk of infection is substantially reduced at the inlet region of passage 24 by closing scalp 12 over passage 24. Thus, there no longer remains a direct passage from the external environment directly down into passage 24. Suturing scalp 12 over passage 24 ensures that direct contamination will be substantially reduced.

Subsequent to drawing needle 32 completely out of cranial region 10, needle 32 can be released from catheter 26 by pulling needle 32 and catheter 26 apart. Simply forcing the release of the detents or serrations causes separation. The serrations found in female coupling means 50 of catheter 26 can then be used to accommodate a Luer-Lok coupling 52 between catheter 26 and adapter 54. Adapter 54 is preferably a Tuohy-Borst ® adapter having a Y-shaped body with means for directing wires 42 in one direction and intracranial fluid in another direction. Wires 42 are directed continuously through adapter 54 in a sealed, liquid-tight and air-tight configuration with a flexible, elastic seal or O-ring 56 placed between wires 42 and the inner surface of adapter 54. Like the Luer-Lok coupling 52, seal 56 prevents intracranial fluids from leaking from adapter 54 to the outside environment. Conversely, Luer-Lok 52 and seal 56 prevents contamination from entering the intracranial fluid environment. Seal 56 can be of any rubber-like, elastic or plastic material which provides a air and fluid-tight seal. A stopcock 58 is configured to pressably seal against the inner diameter surface of one arm of Y-shaped adapter 54. By removing stopcock 58, intracranial fluid can be drained or accessed. Draining is important when fluid pressure becomes excessibly high, while access is necessary to inject dye into the intracranial fluid or visually inspect the fluid for bacteria.

A transducer connector 60 is coupled at the distal end of catheter wires 42 as shown in FIG. 5. Connector 60 includes a socket 62 which is capable of being plugged into a monitor 64. Monitor 64 reads and analyzes the electrical signals coming from transducer tipped catheter 40 as they are transferred along electrical wires 42. Because electrical wires 42 do not lose their signal-carrying integrity when they are bent and closely drawn along the subdermal region, there are no false or bogus readings, artifacts or damping associated with the transferred signals. Furthermore, electrical wires of the present invention do not carry air bubbles as do conventional fluid-filled catheters, nor do wires crimp or pinch-off as in conventional fiber-optic catheters. Thus, the present invention allows high fidelity, highly sensitive readings be obtained at monitor 64 thereby allowing complex measurement of fluid composition, hemodynamics and pressure waveforms directly at the ventricular intracranial region.

Important in the present invention is elongated groove 36 placed in needle 32. Groove 36 allow catheter wires 42 and attached transducer tipped catheter 40 to be passed therethrough while also allowing catheter wires 42 and catheter 26 to be released after needle 32 is withdrawn from cranial region 10. Once needle 32 is separated from catheter wires 42 and catheter 26, a Tuohy-Borst ® adapter 54 is quickly and easily slid over catheter wires 42 and Luer-Lokked to distal end 38 of catheter 26. Once adapter 54 is Luer-Lokked in position, seal 56 is sealingly engaged against the outer surface of wires 42. The entire assembly of the present invention is arranged to thereby prevent fluid leakage or contamination from entering ventricular region of brain 20.

Figure 8:
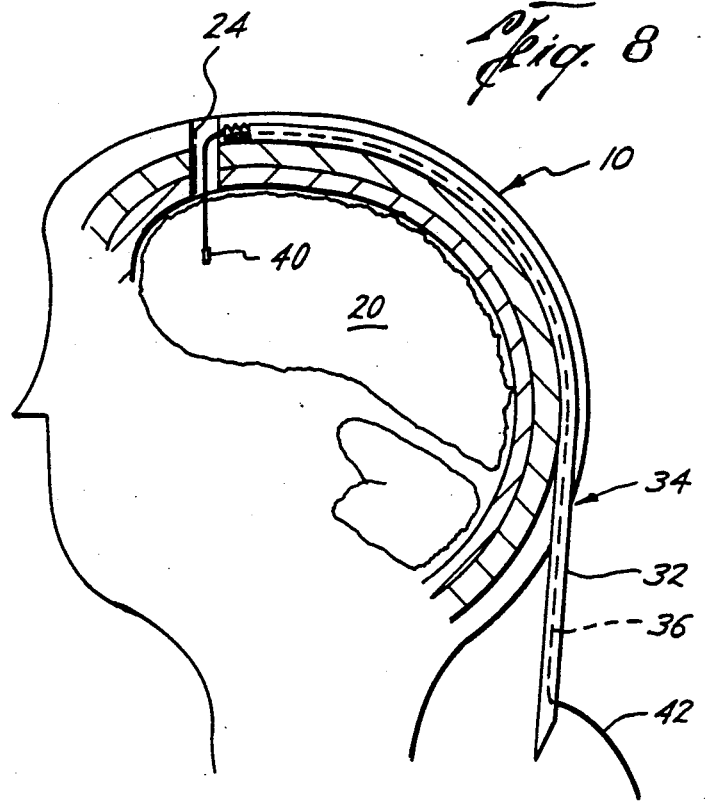
FIG. 8 is a fragmentary anatomical sectional view of the cranial region showing an alternative preferred embodiment having only the distal end of the transducer tipped catheter placed in the burr hole passage; and, FIG. 9 is a fragmentary anatomical sectional view of the cranial region showing transducer tipped catheter placed external to the dura matter.

Turning to FIG. 8, an alternative preferred embodiment is shown wherein the distal tip of transducer tipped catheter 40 is inserted directly into passage 24. This alternative preferred embodiment does not require an in-dwelling catheter for receiving the distal end of transducer tipped catheter 40. Thus, catheter 40 is inserted directly into groove 36 of needle 32 and along groove 36 until it enters passage 24. Transducer tipped catheter 40 can then be manipulated down into passage 24 and within the ventricular region of brain 20. Although not shown, needle 32 may be withdrawn while maintaining the distal end of transducer tip 40 within the ventricular region. Conversely, needle 32 may remain in place if the operator chooses. This form of direct placement of transducer tip 40 into passage 24 provides a quick and simple means for monitoring intracranial pressure directly at the source (i.e., at the ventricular region).

Figure 9:
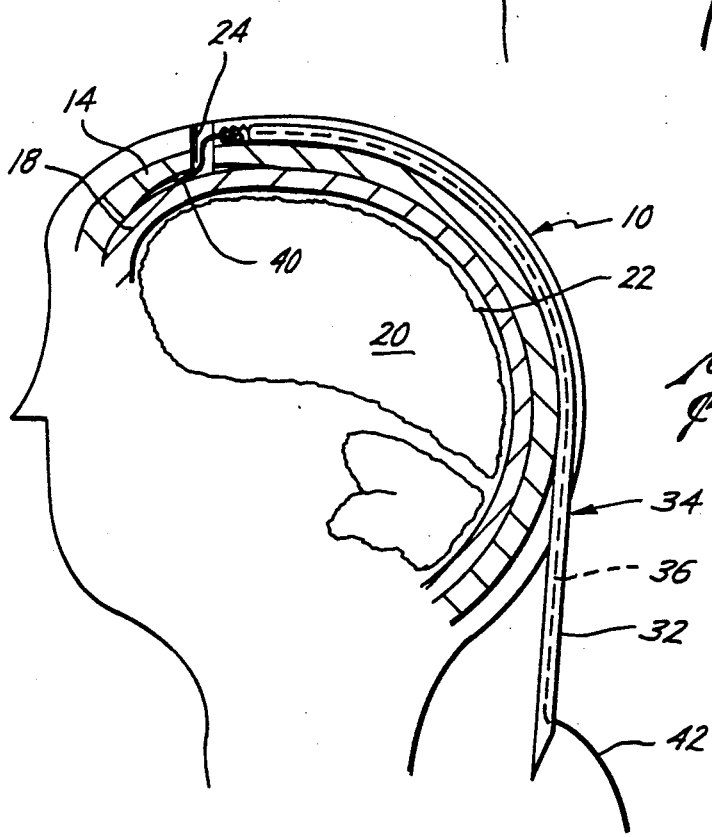

FIG. 9 illustrates an alternative preferred embodiment for measuring intracranial pressure epidurally. In particular, the alternative preferred embodiment of FIG. 9 illustrates the distal end of transducer tip catheter 40 placed between skull 14 and detached dura matter 18. Catheter 40 senses pressure deflection upon dura 18 from cerebral spinal fluid 20 residing on the opposite side of dura 18. Similar to FIG. 8, the distal tip of transducer tip catheter 40 is inserted into distal region 34, through groove 36 of needle 32 and into passage 24. The distal tip of catheter 40 is further inserted between a detached portion of dura 18 and skull 14. Thus, FIG. 9 illustrates another preferred embodiment in which intracranial pressure is measured without penetrating the dura matter. Because dura matter is not severed or cut, the patient is subjected to less risk of contamination entering the unrelying brain 20 through passage 24.

The foregoing description of the present invention has been directed to particular preferred embodiments. It will be apparent, however, to those skilled in the art that modification and changes to the method and assembly may be made without departing from the scope and spirit of the invention. For example, catheters 26 and 40 can be of any size and dimension depending upon the particular application. Further, it is understood that passage 24 is created in the conventional manner with proximal end 30 of catheter 26 quickly and safely inserted into the ventricular region of brain 20. It is certainly possible that distal region 34 can constitute a reentry point back into the vascular system at a distal location similar to a "shunt" arrangement. Furthermore, groove 36 can be of any dimension provided it allows passage of transducer 40 and wires 42 therethrough while also allowing wires 42 to be released from groove 36 after needle 32 is withdrawn from distal region 34. Therefore, it is the applicant's intention in the following claims to cover all such equivalent modifications and variations which fall within the true spirit and scope of this invention.

What is claimed is:

1. An assembly for measuring the fluid characteristics in a region of intercranial fluid, comprising:
   a flexible in-dwelling catheter having a proximal end and a distal end, the distal end having a plurality of openings, wherein the distal end of the in-dwellings catheter is adapted to be placed in communication with said intracranial fluid through a passage in the skull;
   a grooved stainless steel needle adapted to be routed subdermally between the scalp and skull from said passage to an exit point spaced from said passage, and having a proximal end removably attachable to the proximal end of said in-dwelling catheter and a distal end having a beveled point, wherein the distal end of the in-dwelling catheter and the distal end of the needle extend in opposite directions when the two elements are connected;
   a transducer tipped catheter to measure fluid characteristics in a region of intracranial fluid, dimensioned to be positioned through said exit point, through the groove of said needle and to reside within the distal end of said in-dwelling catheter;
   means for connecting said needle to the proximal end of said in-dwelling catheter, so that the needle and the proximal end of said in-dwelling catheter can be drawn out of said exit point; and
   a monitor to analyze fluid characteristics in a region of intracranial fluid, the monitor being electrically connected to said transducer tipped catheter.

2. The assembly as recited in claim 1, wherein said in-dwelling catheter comprises a radiopaque silicone rubber tubing open at the proximal end to accommodate said transducer tipped catheter and closed at the distal end except for said plurality of openings, said transducer tipped catheter having a smaller diameter than said silicone rubber tubing.

3. The assembly as recited in claim 1, wherein said openings are arranged along the side of the distal end of said catheter and are of sufficient diameter to permit flow of fluid.

4. The assembly as recited in claim 1, wherein said needle is shapeable to extend subdermally between the scalp and skull from said passage to said exit point.

5. The assembly as recited in claim 1, wherein the proximal end of said needle comprises a male fitting with snap-fit serration thereon.

6. The assembly as recited in claim 1, wherein the proximal end of said needle comprises a male fitting with detents thereon.

7. The assembly as recited in claim 1, wherein the proximal end of said needle comprises a male fitting with threads thereon.

8. The assembly as recited in claim 1, wherein the proximal end of said in-dwelling catheter comprises a female fitting with serrations thereon.

9. The assembly as recited in claim 1, wherein the proximal end of said in-dwelling catheter comprises a female fitting with detents thereon.

10. The assembly as recited in claim 1, wherein the proximal end of said in-dwelling catheter comprises a female fitting with threads thereon.

11. The assembly as recited in claim 1, wherein the proximal end of said needle and the proximal end of said in-dwelling catheter are releasably pushable together.

12. The assembly as recited in claim 1, wherein the proximal end of said needle and the proximal end of said in-dwelling catheter are releasably rotatable together.

13. The assembly as recited in claim 1, wherein said exit point is positioned at a substantially distant location from said passage.

14. The assembly as recited in claim 1, wherein said exit point is located at a point substantially distant from the cranial region to thereby operate as a shunt for directing intracranial fluid into the vascular system.

15. The assembly as recited in claim 1, further comprising an adaptor means which is coupled to the proximal end of said in-dwelling catheter for allowing access to said intracranial fluid after said catheter is separated from said needle.

16. The assembly as recited in claim 15, wherein said adaptor means comprises a Luer-Lok coupling to said in-dwelling catheter.

17. The assembly as recited in claim 15, wherein said adaptor means comprises a Y-shaped body with one arm of the Y-shaped body having a stopcock for accessing said fluid and the other arm of the Y-shaped body having a seal means for preventing infection from entering said intracranial fluid via transducer tipped catheter extending therethrough.

18. The assembly as recited in claim 1, additionally comprising a stylet for inserting said in-dwelling catheter into the intracranial fluid.

19. The assembly as recited in claim 1, wherein said transducer tipped catheter comprises a strain gauge and electrically connected wires for measuring hemodynamics and pressure waveforms of said intracranial fluid.

20. The assembly as recited in claim 1, wherein said groove is dimensioned to accommodate the diameter of said transducer tipped catheter.

21. The assembly as recited in claim 1, wherein said means for connecting said needle to the proximal end of said in-dwelling catheter is releasable.

* * * * *

UNITED STATES PATENT AND TRADEMARK OFFICE
CERTIFICATE OF CORRECTION

PATENT NO. : 5,191,898
DATED : March 9, 1993
INVENTOR(S) : Huntly D. Millar

It is certified that error appears in the above-indentified patent and that said Letters Patent is hereby corrected as shown below:

In claim 1, column 9, line 13, replace the word "intercranial" with --intracranial--.

In claim 1, column 9, line 16, replace the word "in-dwellings"

Signed and Sealed this

Thirtieth Day of November, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,191,898
DATED : March 9, 1993
INVENTOR(S) : Huntly D. Millar

It is certified that error appears in the above-indentified patent and that said Letters Patent is hereby corrected as shown below:

In claim 1, column 9, line 16, replace the word "in-dwellings" with --in-dwelling--.

Signed and Sealed this

Twenty-fourth Day of May, 1994

Attest:

BRUCE LEHMAN

Attesting Officer    Commissioner of Patents and Trademarks